United States Patent [19]

Bosshard et al.

[11] Patent Number: 4,612,378
[45] Date of Patent: Sep. 16, 1986

[54] PROCESS FOR THE PREPARATION OF β-(BENZOTHIAZOLYLTHIO)- AND β-(BENZIMIDAZOLYLTHIO)-CARBOXYIC ACIDS

[75] Inventors: Hans Bosshard, Basel; Hans Greuter, Eiken, both of Switzerland

[73] Assignee: Ciba-Geigy Corporation, Ardsley, N.Y.

[21] Appl. No.: 610,145

[22] Filed: May 14, 1984

[30] Foreign Application Priority Data

May 14, 1983 [GB] United Kingdom ................ 8313321

[51] Int. Cl.$^4$ ............................................ C07D 277/70
[52] U.S. Cl. ..................................... 548/170; 548/329
[58] Field of Search ................................ 548/170, 329

[56] References Cited

U.S. PATENT DOCUMENTS 2,725,364  11/1955  Dozzi ................................. 548/170
3,499,085   3/1970  Sasse et al. ........................ 548/329
4,289,886   9/1981  D'Amico ............................. 548/170

FOREIGN PATENT DOCUMENTS 0204183  11/1983  Japan ................................. 548/170
149785    9/1962  U.S.S.R. ............................. 548/127

OTHER PUBLICATIONS

F. B. Zienty et al, J. Org. Chem. 27, 3140 (1962).

Primary Examiner—John Kight
Assistant Examiner—Garnette D. Draper
Attorney, Agent, or Firm—Luther A. R. Hall

[57] ABSTRACT

The reaction of 2-mercapto-benzothiazole or -benzimidazole with α,β-unsaturated carboxylic acids in a strongly acid reaction medium gives compounds of the formula I

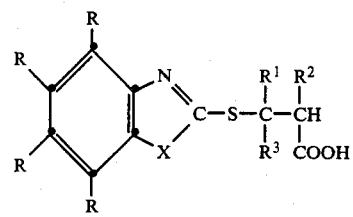

in which X is sulfur or NH, each radical R independently of one another is H, alkyl, halogenoalkyl, alkoxy, alkylthio, alkylsulfonyl, phenyl, alkylphenyl, phenylalkyl, cycloalkyl, halogen, $NO_2$, CN, COOH, COOalkyl, OH or an amino or carbamyl group and $R^1$, $R^2$ and $R^3$ independently of one another are H, alkyl, halogenoalkyl, hydroxyalkyl, alkoxyalkyl, carboxyalkyl, carboxyl or unsubstituted or substituted aryl or aralkyl, or $R^1$ and $R^2$ together are straight-chain or branched alkylene, which can be substituted by 1 or 2 carboxyl groups.

11 Claims, No Drawings

PROCESS FOR THE PREPARATION OF β-(BENZOTHIAZOLYLTHIO)- AND β-(BENZIMIDAZOLYLTHIO-CARBOXYLIC ACIDS

The present invention relates to a process for the preparation of aliphatic or cycloaliphatic carboxylic acids which are substituted in the β-position by a heterocyclic mercapto radical, which comprises reacting an α,β-unsaturated carboxylic acid with a heterocyclic mercaptan in a strongly acid medium.

The addition of mercaptans onto α,β-unsaturated acids is known in principle. However, it is usually carried out in a basic medium or using basic catalysts. It is assumed that the first step in this reaction consists of addition of the mercaptide anion onto the β-carbon atom of the carboxylic acid. F. B. Zienty et al. (J. Org. Chem. 27 (1962), 3140) described the addition of various thiols onto maleic anhydride under basic catalysis. These authors comment that the addition under free radical catalysis gives only moderate yields, and that Lewis acids have no catalysing effect.

U.S. Pat. No. 2,725,364 mentions that maleic acid or fumaric acid can be added onto 2-mercaptobenzothiazole at 30°-60° C. in aqueous-alkaline solution, but no experimental details are given.

However, attempts to add α,β-unsaturated carboxylic acids, in particular maleic acid and fumaric acid, onto 2-mercaptobenzothiazole in an alkaline-aqueous medium at 45°-50° C. have shown that no addition occurs within 100 hours. Surprisingly, however, it has been found that the addition proceeds smoothly in a strongly acid medium and the corresponding β-benzothiazolyl-2-mercaptocarboxylic acids are formed in high yield and purity. The same applies to addition onto 2-mercaptobenzimidazole.

The invention thus relates to a process for the preparation of compounds of the formula I

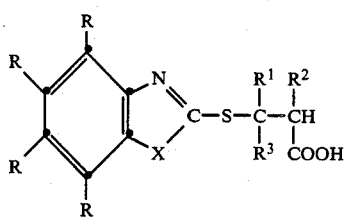

in which X is sulfur or NH, each radical R independently of the others is hydrogen, alkyl, halogenoalkyl, alkoxy, alkylthio, alkylsulfonyl, phenyl, alkylphenyl, phenylalkyl, cycloalkyl, halogen, —NO$_2$, —CN, —COOH, —COOalkyl, —OH or a primary, secondary or tertiary amino or carbamyl group and R$^1$, R$^2$ and R$^3$ independently of one another are hydrogen, alkyl, halogenoalkyl, hydroxyalkyl, alkoxyalkyl, carboxyalkyl, carboxyl or unsubstituted or substituted aryl or aralkyl, or R$^1$ and R$^2$ together are a direct bond or straight-chain or branched alkylene, which can be substituted by 1 or 2 carboxyl groups, by reaction of a mercaptan of the formula II

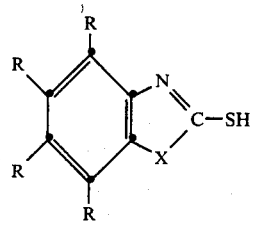

with an unsaturated carboxylic acid of the formula III

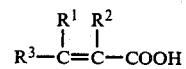

or an anhydride thereof, in a strongly acid medium.

An alkyl radical R in formulae I and II can be straight-chain or branched alkyl and is preferably C$_1$-C$_{12}$-alkyl, for example methyl, ethyl, propyl, isopropyl, n-butyl, isobutyl, tert.-butyl, pentyl, hexyl, octyl, nonyl, decyl or dodecyl. A halogenoalkyl radical R is preferably C$_1$-C$_4$-halogenoalkyl, for example chloromethyl, mono-, di- or tri-fluoromethyl, trichloromethyl or 2-chloroethyl. An alkoxy or alkylthio radical R preferably has 1-4 carbon atoms and can be, for example, methoxy, ethoxy, isopropoxy, methylthio, propylthio or tert.-butylthio. An alkylsulfonyl radical R is preferably C$_1$-C$_{12}$-alkylsulfonyl and can be, for example, methylsulfonyl, tert.-butylsulfonyl, n-octylsulfonyl or n-dodecylsulfonyl.

A cycloalkyl radical R preferably contains 5-8 carbon atoms. Examples are cyclopentyl, cyclohexyl and cyclooctyl. An alkylphenyl or phenylalkyl radical R preferably has 7-12 carbon atoms and can be, for example, tolyl, xylyl, ethylphenyl, tert.-butylphenyl, benzyl, 1- or 2-phenylethyl or α,α-dimethylbenzyl. A —COOalkyl radical R is preferably —COO(C$_1$-C$_4$-alkyl), for example methoxycarbonyl, ethoxycarbonyl or butoxycarbonyl. A primary, secondary or tertiary amino group or carbamyl group R is preferably such a group with up to 20 carbon atoms, for example —NH$_2$, —NHCH$_3$, —NH—C$_4$H$_9$, —NH—phenyl, —NH—cyclohexyl, —N(CH$_3$)$_2$, —N(C$_2$H$_5$)$_2$, —N(i—C$_3$H$_7$)$_2$, —N(CH$_2$CH$_2$OH)$_2$, —N(C$_4$H$_9$)$_2$, —N(C$_8$H$_{17}$)$_2$, —N(CH)$_3$-phenyl, —N(CH$_3$)—benzyl, piperidino, morpholino, —CONH$_2$, —CONHCH$_3$, —CONHphenyl, —CON(CH$_3$)$_2$, —CON(C$_6$H$_{13}$)$_2$, morpholinocarbonyl or piperidinocarbonyl.

A compound of the formula II in which at least two of the substituents R are hydrogen, in particular compounds of the formula II in which one substituent R is hydrogen, C$_1$-C$_4$-alkyl, C$_1$-C$_4$-alkoxy, halogen or —COOH and the other three substituents R are hydrogen, are preferably used.

Compounds of the formula II in which X is sulfur are preferably used, and the corresponding β-(benzothiazol-2-ylthio) carboxylic acids are thereby obtained.

An alkyl substituent R$^1$, R$^2$ or R$^3$ in formulae I and III can be straight-chain or branched alkyl, in particular with 1-12 carbon atoms. Examples are methyl, ethyl, n-propyl, isopropyl, n-butyl, sec.-butyl, isobutyl, n-pentyl, isopentyl, hexyl, heptyl, octyl, nonyl, decyl and dodecyl. A halogenoalkyl or hydroxyalkyl radical R$^1$, R$^2$ or R$^3$ preferably has 1-4 carbon atoms. Examples are hydroxymethyl, 1- or 2-hydroxyethyl, 1-, 2- or 3-hydroxypropyl, 3-hydroxybutyl, chloromethyl, mono-, di- or tri-fluoromethyl, bromomethyl, 2-chloroethyl, 3-chloropropyl and 2-chlorobutyl.

An alkoxyalkyl radical $R^1$, $R^2$ or $R^3$ can be, in particular, $C_2$–$C_{10}$-alkoxyalkyl, for example methoxymethyl, 1- or 2-methoxyethyl, ethoxymethyl, 2-butoxyethyl or octyloxymethyl. A carboxyalkyl radical $R^1$, $R^2$ or $R^3$ can be, in particular, $C_2$–$C_{12}$-carboxyalkyl, for example carboxymethyl, 1- or 2-carboxyethyl, 2- or 3-carboxypropyl, 1- or 4-carboxybutyl or 6-carboxyhexyl. A substituted aryl or aralkyl radical $R^1$, $R^2$ or $R^3$ can be, in particular, phenyl or benzyl which is substituted by halogen, nitro, alkyl, hydroxyl, alkoxy or carboxyl, for example 4-chlorophenyl, 3-nitrophenyl, tolyl, xylyl, 4-tert.-butylphenyl, 4-hydroxyphenyl, 3-methoxyphenyl, 3- or 4-carboxyphenyl, 4-fluorobenzyl or 4-methylbenzyl.

A straight-chain or branched alkylene radical of $R^1$ and $R^2$ together forms, together with the carbon atoms to which $R^1$ and $R^2$ are bonded, a cycloalkane ring, preferably a cyclopentane or cyclohexane ring, which can be substituted by alkyl groups, preferably $C_1$–$C_4$-alkyl groups, or by one or two carboxyl groups.

Preferably, $R^1$, $R^2$ and $R^3$ independently of one another are hydrogen, $C_1$–$C_8$-alkyl, $C_2$–$C_8$-carboxyalkyl, carboxyl or phenyl, or $R^1$ and $R^2$ together are tri-or tetra-methylene. Particularly preferably, at least two of the substituents $R^1$, $R^2$ and $R^3$ are hydrogen.

The mercaptans of the formula II are known compounds or they can be prepared analogously to known compounds. Examples of compounds of the formula II which can be used according to the invention are: 2-mercaptobenzothiazole, 5-methyl-2-mercaptobenzothiazole, 4-isopropyl-2-mercaptobenzothiazole, 7-t-butyl-2-mercaptobenzothiazole, 6-cyclohexyl-2-mercapto-benzothiazole, 7-benzyl-2-mercapto-benzothiazole, 5-trifluoromethyl-2-mercapto-benzothiazole, 6-methoxy-2-mercapto-benzothiazole, 7-ethoxy-2-mercaptobenzothiazole, 4-methylthio-2-mercaptobenzothiazole, 6-methylsulfonyl-2-mercaptobenzothiazole, 4-fluoro-2-mercapto-benzothiazole, 5-chloro-2-mercapto-benzothiazole, 7-bromo-2-mercapto-benzothiazole, 6-chloro-2-mercapto-benzothiazole, 4-phenyl-2-mercapto-benzothiazole, 6-nitro-2-mercapto-benzothiazole, 5-cyano-2-mercapto-benzothiazole, 5-carboxy-2-mercapto-benzothiazole, 5-methoxycarbonyl-2-mercapto-benzothiazole, 7-hydroxy-2-mercapto-benzothiazole, 6-amino-2-mercapto-benzothiazole, 5-dimethylamino-2-mercapto-benzothiazole, 5-morpholino-2-mercapto-benzothiazole, 5-carbamyl-2-mercapto-benzothiazole, 5-phenylcarbamyl-2-mercapto-benzothiazole, 5-chloro-6-n-butyl-2-mercaptobenzothiazole, 5-nitro-6-n-propyl-2-mercapto-benzothiazole, 5-bromo-6-n-propoxy-2-mercapto-benzothiazole, 4,5,6-triethyl-2-mercapto-benzothiazole, 4,5,6,7-tetramethyl-2-mercapto-benzothiazole, 4-methoxy-6-hydroxy-2-mercapto-benzothiazole, 4,5-dimethyl-7-propoxy-2-mercapto-benzothiazole, 2-mercaptobenzimidazole, 6-methyl-2-mercapto-benzimidazole, 4-isopropyl-2-mercapto-benzimidazole, 5-n-hexyl-2-mercapto-benzimidazole, 6-(1,1,3,3-tetramethylbutyl)-2-mercapto-benzimidazole, 7-benzyl-2-mercapto-benzimidazole, 6-ethoxy-2-mercapto-benzimidazole, 6-isopropoxy-2-mercaptobenzimidazole, 4-fluoro-2-mercapto-benzimidazole, 5-chloro-2-mercapto-benzimidazole, 5-chloro-2-mercapto-benzimidazole, 5-cyano-2-mercapto-benzimidazole, 4-phenyl-2-mercapto-benzimidazole, 6-nitro-2-mercapto-benzimidazole, 5-carboxy-2-mercapto-benzimidazole, 5-butoxycarbonyl-2-mercapto-benzimidazole, 7-hydroxy-2-mercapto-benzimidazole, 6-amino-, 5-dimethylamino-, 4-piperidino-, 5-methylcarbamyl- or 5-diethylcarbamyl-2-mercapto-benzimidazole, 4-bromo-5-n-hexyl-2-mercapto-benzimidazole, 5-nitro-6-n-propyl-2-mercaptobenzimidazole, 4,5,6-triethyl-2-mercapto-benzimidazole and 4,5-dimethyl-7-propoxy-2-mercapto-benzimidazole.

Examples of unsaturated carboxylic acids of the formula III are: acrylic acid, methacrylic acid, crotonic acid, 2,3- or 3,3-dimethylacrylic acid, propiolic acid, phenylpropiolic acid, maleic acid, fumaric acid, acetylene dicarboxylic acid, itaconic acid, cyclohexene-1,2-dicarboxylic acid, 3-methylcyclohexene-1,2-dicarboxylic acid, ethylenetetracarboxylic acid, mesaconic acid, glutaconic acid, aconitic acid, citraconic acid, α-methyleneglutaric acid, α-methyleneadipic acid, α-ethylidene-adipic acid, propylene-1,3-dicarboxylic acid, 1-butene-1,4-dicarboxylic acid, 1-butene-2,3,4-tricarboxylic acid, 2-pentenoic acid, 2-hexenoic acid, 2-octenoic acid, 2-decenoic acid, 2-undecenoic acid, 2-dodecenoic acid, 2-octadecenoic acid, cinnamic acid, α-phenylacrylic acid, α-phenylcrotonic acid, β-benzylacrylic acid, benzylidenemalonic acid, α-methylcinnamic acid, 4-chlorocinnamic acid and 3-nitrocinnamic acid.

Instead of the carboxylic acid, it is also possible to use anhydrides thereof. When the reaction is carried out in an aqueous medium, the carboxylic acid of the formula I is obtained as the product. If the reaction is carried out in an anhydrous medium, the corresponding anhydride is first obtained, and can easily be subsequently hydrolysed to the carboxylic acid. Such a hydrolysis usually already occurs on dilution with water. The anhydrides used as the reaction components can be those of a monocarboxylic acid, for example acrylic anhydride or methacrylic anhydride. The use of anhydrides is of particular interest in the case of 1,2-dicarboxylic acids. Examples of such anhydrides are maleic anhydride, itaconic anhydride and citraconic anhydride, as well as cyclohexene-1,2-dicarboxylic acid anhydride.

A dicarboxylic or polycarboxylic acid of the formula III in which $R^3$ is carboxyl or $R^2$ is carboxymethyl, or the cyclic anhydride of such a compound, is preferably used as the carboxylic acid. Maleic acid or maleic anhydride is particularly preferably used.

The reaction of II with III is carried out in a strongly acid medium. The reaction medium can be, for example, an aqueous solution of a mineral acid, for example of $H_2SO_4$, $H_3PO_4$, HCl, HBr, $HBF_4$, $HClO_4$, $H_2S_2O_7$ or polyphosphoric acid. Organic acids, for example formic acid, trifluoroacetic acid or p-toluenesulfonic acids, can be used in aqueous solution or in organic solution. Certain acids can also serve as the reaction medium in undiluted form, for example trifluoroacetic acid, formic acid or phosphoric acid.

Lewis acids, for example $AlCl_3$, $AlBr_3$, $BF_3$, $SbF_5$, $SbCl_5$ or $SnCl_4$, can also be used as the acids. In this case, the reaction is carried out in an inert solvent in which the Lewis acid is soluble, for example in diethyl ether or in halogenated hydrocarbons.

If the starting materials are insoluble in the aqueous acid used, it is also possible to add a water-miscible organic solvent, for example methanol, ethanol, ethylene glycol monomethyl ether, acetic acid, propionic acid, tetramethylenesulfone (sulfolane), tetrahydrofuran, dioxane, acetone or dimethylsulfoxide. In this case, the reaction is thus carried out in an acid aqueous-organic medium.

The reaction is preferably carried out in an aqueous or aqueous-organic solution of a strong proton acid, in particular in 60–90% sulfuric acid or in 25–38% hydrochloric acid.

The reaction temperature can be in the range from −30° C. up to the boiling point of the reaction medium, and is preferably 0° to 100° C. Under certain conditions, it may be advantageous to carry out the reaction under increased pressure, but this is not necessary.

The reaction components are used in the approximate molar ratio of 1:1, a slight excess of up to about 10 mol % of the carboxylic acid III being employed. One component can first be dissolved or dispersed in the acid reaction medium and the second component can then be added. Alternatively, the two components are first mixed and this mixture is introduced slowly into the acid reaction medium.

The products can be isolated by customary methods. If a concentrated mineral acid is used, it is advantageous to dilute the reaction mixture with water after the reaction has ended and to neutralise some of the mineral acid by addition of a base, such as NaOH or NaCO₃, in which case the product usually precipitates after cooling or can be isolated by extraction. The crude product can be purified by reprecipitation from an aqueous base. In general, the products precipitate in a high purity by the process according to the invention, so that further purification is frequently unnecessary.

The compounds of the formula I can be used as corrosion inhibitors in aqueous systems or in coating agents for metals. The invention is illustrated in more detail by the following examples. The temperatures in the examples are given in °C.

EXAMPLE 1

16.8 g of finely powdered 2-mercaptobenzothiazole are suspended in 40 ml of 70% sulfuric acid, and 10.2 g of powdered maleic anhydride are added at 48°–51° in the course of 1 hour, with stirring. After a further hour at 50°, the reaction mixture is cooled to room temperature and is diluted by dropwise addition of 250 ml of water at 25°–35°. After 1 hour, the precipitated product is filtered off and dissolved in dilute sodium hydroxide solution. The solution is filtered and the filtrate is acidified with hydrochloric acid. The precipitate is filtered off and dried at 60° in vacuo. 24.7 g (87% of theory) of benzothiazol-2-ylthiosuccinic acid of melting point 175°–176°, with decomposition, are thus obtained.

Analysis ($C_{11}H_9NO_4S_2$). Calculated: 46.64% C; 3.18% H; 4.94% N; 22.61% S. Found: 46.6% C; 3.4% H; 5.0% N; 22.5% S.

If the same reaction is carried out with 12.1 g of maleic acid instead of the anhydride, 22.6 g (80% of theory) of benzothiazolylthiosuccinic acid are obtained.

If the same reaction is carried out with 12.1 g of fumaric acid and the components are reacted at 40° for 12 hours, 21.1 g (75% of theory) of benzothiazolylthiosuccinic acid are obtained.

EXAMPLE 2

A finely powdered mixture of 16.8 g of 2-mercaptobenzothiazole and 10.3 g of maleic anhydride are added to a mixture of 60 ml of 36% hydrochloric acid and 60 ml of 99% acetic acid, with stirring. The reaction mixture is then warmed at 70°–75° for 4 hours and the solution is poured into 500 ml of water. The precipitate is filtered off, washed with cold water and dried. 24 g (85% of theory) of benzothiazol-2-ylthiosuccinic acid are obtained.

EXAMPLE 3

3.4 g of 2-mercaptobenzothiazole and 2.0 g of maleic anhydride are heated at 50° in 40 ml of trifluoroacetic acid for 12 hours, with stirring. The reaction mixture is diluted with ice-water and the precipitated product is taken up in ethyl acetate. The solution is washed 3 times with water and evaporated to dryness. 4.5 g (79% of theory) of benzothiazol-2-ylthiosuccinic acid are obtained.

EXAMPLE 4

16.8 g of powdered 2-mercaptobenzothiazole are suspended in 50 ml of 70% sulfuric acid, and 13.7 g of itaconic acid are stirred into this suspension at 40°–44° in the course of 30 minutes. After a further 1.5 hours at 40°–44°, the reaction mixture is cooled to room temperature and diluted with water, the temperature being kept below 35°. The precipitated 3-(benzothiazol-2-ylthio)-propane-1,2-dicarboxylic acid is filtered off, washed with cold water and dried at 60° in vacuo. Yield: 27.5 g (92% of theory), melting point: 160°–166°.

Analysis ($C_{12}H_{11}NO_4S_2$). Calculated: 48.48% C; 3.73% H; 4.71% N; 21.57% S. Found: 48.2% C; 3.7% H; 4.6% N; 21.3% S.

If the addition of itaconic acid onto 2-mercaptobenzothiazole is carried out in trifluoroacetic acid in a manner similar to that in Example 3, 3-(benzothiazol-2-ylthio)-propane-1,2-dicarboxylic acid is obtained in 96% yield.

EXAMPLE 5

13.3 g of $AlCl_3$ are dissolved in 100 ml of diethyl ether at 0° to 5°. 3.4 g of 2-mercaptobenzothiazole and 2.6 g of itaconic acid are then added. After the mixture has been stirred at 20°–25° for 24 hours, the ether solution is poured off and the residue is stirred with 100 ml of water and 100 ml of ethyl acetate. The organic phase is separated off, dried and evaporated. 3 g of 3-(benzothiazol-2-ylthio)-propane-1,2-dicarboxylic acid are obtained as the residue.

EXAMPLE 6

16.8 g of 2-mercaptobenzothiazole are suspended in 50 ml of 70% $H_2SO_4$, and 13.7 g of glutaconic acid are added at 45°–50° in the course of 30 minutes, with stirring. The reaction mixture is stirred for a further 1.5 hours at 45°–50° and the product is isolated as described in Example 5. 26 g (88% of theory) of 3-(benzothiazol-2-ylthio)-glutaric acid, of melting point 153°–154°, are obtained.

Analysis ($C_{12}H_4NO_4S_2$). Calculated: 48.48% C; 3.71% H; 4.71% N; 21.57% S. Found: 48.5% C; 3.8% H; 4.6% N; 21.2% S.

EXAMPLE 7

16.8 g of finely powdered 2-mercaptobenzothiazole are suspended in 50 ml of 70% aqueous sulfuric acid. 9.0 g of methacrylic acid are added dropwise at 45° to 50° in the course of 30 minutes, with thorough stirring. The mixture is kept at 50° for 1 hour and is then diluted at 20°–35° by dropwise addition of 250 ml of water. The precipitated product is dissolved in water, with the addition of sodium hydroxide solution, and insoluble constituents are removed by filtration. The product is precipitated from the filtrate by addition of hydrochloric acid and is isolated. After drying at 60° in vacuo, 22.3 g (88% of theory) of 3-(benzothiazol-2-ylthio)-propane-2-carboxylic acid of melting point 97°–99°, after recrystallisation from cyclohexane/hexane 1:1, are obtained.

Analysis ($C_{11}H_{11}NO_2S_2$). Calculated: 52.15% C; 4.38% H; 5.53% N; 25.31% S. Found: 52.3% C; 4.4% H; 5.7% N; 25.7% S.

2-(Benzothiazol-2-ylthio)-propane-1-carboxylic acid of melting point 61°–63° after recrystallisation from cyclohexane/hexane 1:1, is obtained in a similar manner using crotonic acid instead of methacrylic acid.

EXAMPLE 8

47.4 g of 2-mercaptobenzimidazole and 40.7 g of itaconic acid, mixed in finely powdered form, are introduced into 150 ml of 70% aqueous sulfuric acid in the course of 1 hour. The temperature is kept at 40° to 43°, with stirring. The mixture is then allowed to react completely at the above temperature over a period of 1½ hours and the reaction mixture is diluted with water and ice to about 2 liters. The product is precipitated by addition of 30% aqueous sodium hydroxide solution to pH 4 and filtered off. After washing with water and drying in vacuo at about 30°, 92.5 g of 3-(benzimidazol-2-ylthio)-propane-1,2-dicarboxylic acid are obtained in the form of a dihydrate of melting point 113° (decomposition), corresponding to 97% of theory.

The anhydrous product of melting point 165°–168° is obtained by recrystallisation from acetone.

Analysis ($C_{12}H_{12}N_2O_4S$). Calculated: 51.42% C; 4.32% H; 10.00% N; 11.44% S. Found: 51.6% C; 4.4% H; 9.8% N; 11.2% S.

Benzimidazol-2-ylthiosuccinic acid of melting point 212° (with decomposition) is obtained in a similar manner using maleic anhydride instead of itaconic acid.

EXAMPLE 9

15.0 g of 2-mercaptobenzimidazole are dissolved in 50 ml of 70% aqueous sulfuric acid. 9.0 g of acrylic acid are added dropwise at 20° to 25° in the course of about 1 hour. The mixture is kept at 20° to 25° for 2 hours and is then diluted with ice-water to about 250 ml. The pH value is adjusted to about 5 by addition of sodium hydroxide solution and the product is filtered off, washed with water and dried. 22.0 g (99% of theory) of 2-(benzothiazol-2-ylthio)-propionic acid of melting point 188° (decomposition), after recrystallisation from glacial acetic acid, are obtained.

Analysis ($C_{10}H_{10}N_2O_2S$). Calculated: 54.04% C; 4.54% H; 12.6% N; 14.43% S. Found: 54.3% C; 4.5% H; 12.5% N; 14.1% S.

If 10.8 g of methacrylic acid are used instead of the acrylic acid and the reaction is carried out at 50°, 1-(benzimidazol-2-ylthio)-propane-2-carboxylic acid of melting point 175°–176° is obtained.

If 10.8 g of crotonic acid are used in a similar manner and the reaction is carried out at 55°, 2-(benzimidazol-2-ylthio)-propane-1-carboxylic acid of melting point 153°–155°, after recrystallisation from ethanol/water 1:3, is obtained.

EXAMPLE 10

4.45 g of 2-mercaptobenzothiazole and 5 g of but-3-ene-1,2,3-tricarboxylic acid are ground together in a mortar. The powdered mixture is introduced in portions into 60 ml of 70% $H_2SO_4$ at 48°–50° in the course of 1 hour, with stirring. After a further 3 hours at 48°–50°, the reaction mixture is cooled to room temperature and diluted with 250 ml of water at 25°–30°, with stirring. The aqueous solution is decanted from a little glutinous sediment and diluted with a further 200 ml of water. After stirring for 1 hour, the precipitate is filtered off and dried. The 4-(benzothiazol-2-ylthio)-butane-1,2,3-tricarboxylic acid obtained has a melting point of 188°–190°, after recrystallisation from methanol/water.

Analysis ($C_{14}H_{13}NO_6S_2$). Calculated: 47.32% C; 3.69% H; 3.94% N. Found: 47.40% C; 3.86% H; 3.89% N.

EXAMPLE 11

8.6 g of 6-chloro-2-mercapto-4-methylbenzothiazole are reacted with 4.4 g of maleic anhydride in 70% $H_2SO_4$ at 47°–50° as described in Example 1. The crude product is purified by reprecipitation from $NaHCO_3$ solution. 6-Chloro-4-methylbenzothiazol-2-ylthiosuccinic acid of melting point 168°–171°, with decomposition, is obtained.

Analysis ($C_{12}H_{10}ClNO_4S_2$). Calculated: 43.44% C; 3.04% H; 4.22% N. Found: 53.48% C; 3.20% H; 4.17% N.

5-Carboxybenzothiazol-2-ylthiosuccinic acid of melting point 210°–215°, with decomposition, is obtained in a similar manner from 20 g of 5-carboxy-2-mercaptobenzothiazole and 10.26 g of maleic anhydride.

Analysis ($C_{12}H_9NO_6S_2$). Calculated: 44.04% C; 2.78% H; 4.28% N. Found: 43.9% C; 2.78% H; 4.39% N.

What is claimed is:

1. A process for the preparation of a compound of the formula I

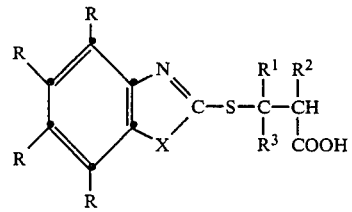

in which X is sulfur or NH, each radical R is the same or different from each other radical R and is hydrogen, alkyl, halogenoalkyl, alkoxy, alkylthio, alkylsulfonyl, phenyl, alkylphenyl, phenylalkyl, cycloalkyl, halogen, —$NO_2$, —CN, —COOH, —COOalkyl, —OH or a primary, secondary or tertiary amino or carbamyl group and $R^1$, $R^2$ and $R^3$ are all the same or different and are hydrogen, alkyl, halogenoalkyl, hydroxyalkyl, alkoxyalkyl, carboxyalkyl, carboxyl or unsubstituted or substituted aryl or aralkyl, or $R^1$ and $R^2$ together are a direct bond or straight-chain or branched alkylene, which can be substituted by 1 or 2 carboxyl groups, by reaction of a mercaptan of the formula II

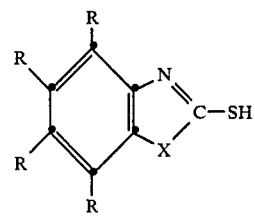

with an unsaturated carboxylic acid of the formula III

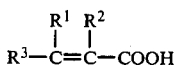

or an anhydride thereof, in a strongly acid medium.

2. A process according to claim 1, wherein the reaction medium is the aqueous or organic-aqueous solution of a strong proton acid.

3. A process according to claim 2, wherein the reaction medium is 60–90% sulfuric acid or 25–38% hydrochloric acid.

4. A process according to claim 1, wherein the reaction is carried out at a temperature of 0° C. to 100° C.

5. A process according to claim 1, wherein a mercaptan of the formula II in which at least two of the substituents R are hydrogen is used.

6. A process according to claim 5, wherein one of the radicals R is hydrogen, $C_1$–$C_4$-alkyl, $C_1$–$C_4$-alkoxy, halogen, —COOH or an amino group and the other three radicals R are hydrogen.

7. A process according to claim 1, wherein a compound of the formula II in which X is sulfur is used.

8. A process according to claim 1, wherein a carboxylic acid of the formula III in which $R^1$, $R^2$ and $R^3$ are all the same or different and are hydrogen, $C_1$–$C_8$-alkyl, $C_2$–$C_8$-carboxyalkyl, carboxyl or phenyl, or $R^1$ and $R^2$ together are tetramethylene is used.

9. A process according to claim 1, wherein a carboxylic acid of the formula III in which at least two of the substituents $R^1$, $R^2$ and $R^3$ are hydrogen is used.

10. A process according to claim 1, wherein a carboxylic acid of the formula III in which $R^3$ is carboxyl or $R^2$ is carboxymethyl, or the cyclic anhydride of such a compound, is used.

11. A process according to claim 10, wherein a compound of the formula II is reacted with maleic acid or maleic anhydride in a strongly acid medium.

* * * * *